United States Patent
Ertl

(10) Patent No.: US 9,101,329 B2
(45) Date of Patent: Aug. 11, 2015

(54) METHOD FOR DETERMINING THE POSITION OF AN INTRAORAL MEASURING DEVICE

(75) Inventor: Thomas Ertl, Florstadt (DE)

(73) Assignee: DEGUDENT GMBH, Hanau (DE)

( * ) Notice: Subject to any disclaimer, the term of this patent is extended or adjusted under 35 U.S.C. 154(b) by 601 days.

(21) Appl. No.: 12/677,601

(22) PCT Filed: Sep. 12, 2008

(86) PCT No.: PCT/EP2008/062116
§ 371 (c)(1),
(2), (4) Date: May 3, 2010

(87) PCT Pub. No.: WO2009/034157
PCT Pub. Date: Mar. 19, 2009

(65) Prior Publication Data
US 2010/0239996 A1  Sep. 23, 2010

(30) Foreign Application Priority Data
Sep. 12, 2007 (DE) .......................... 10 2007 043 366

(51) Int. Cl.
*A61C 1/00* (2006.01)
*A61B 6/00* (2006.01)
(Continued)

(52) U.S. Cl.
CPC ................. *A61B 6/547* (2013.01); *A61B 6/145* (2013.01); *A61B 19/46* (2013.01); *A61B 19/5244* (2013.01); *A61C 19/043* (2013.01); *A61B 2017/00022* (2013.01); *A61B 2017/00026* (2013.01); *A61B 2017/00221* (2013.01);
(Continued)

(58) Field of Classification Search
CPC ................. A61B 19/5244; A61B 2017/00221; A61B 2019/5248; A61B 2019/5295; A61B 6/547; G01B 11/14
USPC ................. 433/27, 29, 31, 69, 103–109, 131; 600/407, 589; 455/41.3
See application file for complete search history.

(56) References Cited

U.S. PATENT DOCUMENTS

| 4,673,352 A | * | 6/1987 | Hansen ........................... 433/69 |
| 5,100,318 A | | 3/1992 | Demyun et al. |

(Continued)

FOREIGN PATENT DOCUMENTS

| DE | 3836743 | 4/1990 |
| DE | 19854223 | 3/2000 |

(Continued)

OTHER PUBLICATIONS

Japanese Office Action mailed Jul. 2, 2013 corresponding to Japanese Patent Application No. 2010-524495; with English language translation.

*Primary Examiner* — Cris L Rodriguez
*Assistant Examiner* — Mirayda A Aponte
(74) *Attorney, Agent, or Firm* — Ladas & Parry LLP

(57) ABSTRACT

A method for determining the position of an intraoral measuring device which is to be moved relative to an organ of mastication of a patient and with which positions in the organ of mastication or areas of the organ of mastication are measured. To be able to carry out measurements without a fixed reference, it is proposed that, independently of a reference that is independent of the patient, the position of the measuring device is measured by means of a position-determining sensor that is in a fixed relationship to the measuring device.

35 Claims, 4 Drawing Sheets

(51) Int. Cl.
   *A61B 6/14* (2006.01)
   *A61B 19/00* (2006.01)
   *A61C 19/04* (2006.01)
   *A61B 17/00* (2006.01)

(52) U.S. Cl.
   CPC ... *A61B2019/462* (2013.01); *A61B 2019/5206* (2013.01); *A61B 2019/528* (2013.01); *A61B 2019/5248* (2013.01); *A61B 2019/5251* (2013.01); *A61B 2019/5289* (2013.01); *A61B 2019/5295* (2013.01)

(56) References Cited

U.S. PATENT DOCUMENTS

| | | | |
|---|---|---|---|
| 5,587,284 A * | 12/1996 | Brattesani | 433/72 |
| 5,755,571 A * | 5/1998 | Companion | 433/72 |
| 5,842,858 A * | 12/1998 | Truppe | 433/69 |
| 5,897,509 A * | 4/1999 | Toda et al. | 600/589 |
| 6,381,485 B1 | 4/2002 | Hunter et al. | |
| 2001/0023057 A1 * | 9/2001 | Alexander | 433/29 |
| 2002/0183959 A1 | 12/2002 | Savill et al. | |
| 2003/0143510 A1 * | 7/2003 | Berube-Lauziere et al. | 433/29 |
| 2003/0204150 A1 * | 10/2003 | Brunner | 600/590 |
| 2005/0020910 A1 | 1/2005 | Quadling et al. | |
| 2005/0100866 A1 * | 5/2005 | Arnone et al. | 433/215 |
| 2006/0030771 A1 * | 2/2006 | Levine et al. | 600/424 |
| 2006/0212260 A1 | 9/2006 | Kopelman et al. | |
| 2007/0065782 A1 * | 3/2007 | Maschke | 433/224 |
| 2007/0264609 A1 * | 11/2007 | Brunner et al. | 433/69 |

FOREIGN PATENT DOCUMENTS

| | | |
|---|---|---|
| DE | 10045381 | 4/2002 |
| EP | 0286067 | 10/1988 |
| EP | 0951874 | 10/1999 |
| EP | 1088525 | 4/2001 |
| WO | 9608209 A2 | 3/1996 |
| WO | 2004100067 A2 | 11/2004 |

* cited by examiner

METHOD FOR DETERMINING THE POSITION OF AN INTRAORAL MEASURING DEVICE

FIELD OF THE INVENTION

The invention relates to a method for determining the position of a measuring device performing measurements intraorally, which is to be moved relative to the craniomandibular system of a patient and which measures positions within the craniomandibular system or regions of the craniomandibular system, whereby the position of the measuring device is measured by means of an inertial platform that is in a stationary position relative to the measuring device. The invention further relates to a method and arrangements for evaluating and measuring the position and pocket depth of periodontal pockets.

BACKGROUND OF THE INVENTION

Known from EP-A-1 733 693 (Goldbach) is a medical tracking system with infrared-based operation. However, just like other systems (e.g. EP-A-1 523 950 (Foley)), it requires an additional stand with infrared receivers and transmitters in the operating room for referencing. These systems link data from imaging systems with the positional information of the navigation system for positioning instruments for stereotactic surgery, e.g. in neurosurgery.

There are first published reports on the use in dentistry of the above-mentioned systems for implant positioning (Mischkowski et al: *Comparison of static and dynamic computer-assisted guidance methods in implantology*, in *Int. J. Comput. Dent.* 2006 January; 9(1): 23-35). Here as well, image data is linked with navigational data in order to define the drilling direction for the implant.

Marmulla R, et al: *Intraoperative precision of mechanical, electromagnetic, infrared and laser-guided navigation Systems in computer-assisted surgery*, in *Mund Kiefer Gesichtschirurgie*, 1998 May; 2 Suppl. 1; pages 145-8, describes the use of a navigation system operating on an electromagnetic basis. However, there have been critical comments regarding the lack of precision of the results in the presence of metallic objects.

During intraoral scanning of teeth, the visible portion of a tooth or jaw section, from which 3D data is to be measured, is usually much smaller than the entire tooth or jaw, making it necessary to combine several images from different viewing directions to create a complete data set of the tooth or jaw region.

The difficulty of precisely determining the positions of regions of the craniomandibular system, i.e. mandible and maxilla, teeth, as well as other interesting regions such as pockets, has its roots in the fact that not only do maxilla and mandible move relative to each other, but the hand-guided scanner moves relative to the jaw and the patient's head is in motion as well. In addition, images of jaw regions are recorded from various angles and viewpoints so that errors can not be ruled out even when employing mature merging software.

Even state-of-the-art software-based fitting-together or merging of individual images is complicated by the fact that teeth do not possess precisely defined corners and edges. If furthermore the positional relation of the pictures relative to each other (camera position) is not known, the computational effort can be quite significant, e.g. noticeably longer than 30 minutes for the Intraoral Scanning System of the firm CaDent, since the algorithms converge only slowly in the case of completely unknown camera position and uncooperative dental geometries.

The evaluation of the electronic impression and the decision, whether the process may have to be repeated, result in unacceptably long waiting times for both the dental professional and the patient.

In order to circumvent this problem, reference objects may be introduced into the mouth (U.S. Pat. No. 7,065,243). During the intraoral measuring of one or several teeth in the presence of a reference, the reference pinpoints the position of a camera that is used to measure the tooth or teeth. Once the camera position relative to the tooth or teeth is known, the measurements are used to generate a 3D model that is needed for the manufacture of dental prostheses. A method of this type is complicated and in addition has the disadvantage that the reference is embodied as an open cuboid box that casts shadows onto the tooth or teeth.

US-A-2003/0219148 also relates to a method for generating a three-dimensional model of a dental arch with the aid of three-dimensional referencing.

A method for intraoral scanning is also known from US-A-2006/0212260. Used for this is a scanner that comprises an inertial or tracking system to determine orientation and position.

An intraoral measuring system according to US-A-2005/0020910 features the option of integrating both a scanner as well as a receiver attached to the patient's head with a three-dimensional tracking system.

DE-B-100 45 381 relates to a device for determining the position of a medical instrument, or apparatus, or body part. For this purpose, the object whose position is to be determined is equipped with active and passive reference bodies, so that a navigational system can determine the position. In this, it is possible to employ inclination-measuring as well as magnetic-field sensors.

Disclosed in EP-A-1 088 525 are a method and a device for aligning medical images on a patient. Provided for this purpose are holder elements, which can be connected to the patient's body and are equipped with marking or localizing means. The purpose is to provide a three-dimensional localizing system for computer-assisted surgery, in order to facilitate the alignment relative to medical surgical procedures.

State of the art measurements of the depth of periodontal pockets or for the diagnostic of dental caries do not use any augmentation with positional data. Consequently, automatic processes for transmitting the measured data into the patient management system of the dental clinic are not possible.

Today's work in diagnosing periodontal diseases is performed by inserting the measuring probe manually into the gingival pocket and by reading a scale on the probe to determine the depth. From the location of the measuring, the doctor communicates a value to the assistant, who then records the corresponding data in dependence on the tooth or position of the measurement relative to a tooth. This entails high costs in both time and personnel.

In the diagnostics of dental caries as well, the diagnosis including the tooth position is verbally transmitted or is entered into the clinic's computer by the treatment professional him/herself. Not only does this entail a great deal of lost time, but there are also hygienic concerns, since while working on a patient one also has to operate a keyboard, which is hard to maintain in a sufficiently sterile state.

Known in the art is only one electromechanical apparatus for determining the pocket depth, which however does not determine any positional data (Florida probe; www.floridaprobe.de). The pocket depth is determined by a mechanical back stop, through which the pin-shaped probe slides until it touches the bottom of the pocket. The path traveled by the pin on its way to the pocket bottom is converted to an electrical signal dependent on a change in opening angle of a mechanical expansion device and is then transmitted to a PC. At least in case of the Florida probe, PC speech input reduces the risk of contamination from the keyboard.

Disclosed in DE-A-37 12 054 is a measuring probe for acquiring the depth of gingival pockets. Also employed in this can be inductive or optical detecting elements, which also include the use of light guides.

In accordance with U.S. Pat. No. 5,100,318, the depth of the gingival pockets is measured by means of ultrasound. The same is true for U.S. Pat. No. 5,755,571, which proposes an ultrasound measuring apparatus to measure the pocket depth. Also provided is the option of measuring the position of the tip of the measuring device relative to the pocket by means of a sensor.

Described in DE-C-38 36 743 is a capacitive measuring method for determining the accuracy-of-fit of dental prostheses such as crowns and bridges.

For the purpose of determining the distance between a crown and the tip of a dental root, DE-A-198 54 223 proposes a device that is used to generate first and second measuring signals, from which the position is determined.

The present invention is based on the objective to further develop a method for determining the position of a first sensor, which is movable relative to a patient's craniomandibular system and which is used to measure positions in the craniomandibular system or regions of the craniomandibular system, particularly positions at or of teeth and/or regions of gingival pockets, in a manner so as to eliminate the need for any referencing systems existing independent of the patient, in particular a referencing system to be mounted on a stand in the treatment room. The method also should be insensitive to metals in the oral cavity. Furthermore, in comparison to state-of-technology solutions, the data amount to be processed is to be reduced without any accompanying decrease in accuracy. The measurements should be safe from falsification due to movement of the patient during the measurements.

When employing an intraoral scanner as a sensor, the combining of partial measurement data into a consistent 3D data set is to be accelerated by providing coarse positional data.

A further objective is to facilitate preferably fully automatic data acquisition during pocket-depth measurements and/or the detection of dental caries or plaque, particularly if a starting position of the measurements is known.

In accordance with the invention, at least some aspects of the above-described problem are overcome by determining positional data of the measuring device by additionally taking into account at least one second inertial platform arranged in stationary relation to the maxilla of the craniomandibular system, whereby in particular after the triggering of a starting signal the positional data of the two inertial platforms are evaluated synchronously.

In accordance with a proposed independent solution, the invention intends that the determination of the position of the measuring device by means of the inertial platform be performed in relation to a starting signal chosen as a starting point. The starting signal may be of a spatial nature, i.e. possess a stationary location relative to the craniomandibular system.

Starting from a first determination of position, which for example may take place at a set starting point as a reference point, one subsequently determines changes in the positional data of the measuring device by means of further measurements spaced over time.

In this, the changes in position of the measuring device are determined by means of an inertial platform, which is present or integrated in—or has a known spatial relation to—the measuring device. Measured are three degrees of freedom of translation and three degrees of freedom of rotation, which enables one to pinpoint the change in location of the scanning sensor relative to the craniomandibular system of the patient. Preferably, the change in position takes place taking into account data of a second inertial platform, which is arranged in a stationary location relative to the maxilla.

According to the invention, the new position relative to the first measurement is computed by integrating the movement changes. Any tilting in space can be measured directly, if necessary.

In this, the invention's solution does not operate by incorporating data that has been obtained by means of imaging processes, but rather is able to create three-dimensional imaging data on its own.

The use of an inertial platform can involve disadvantages related to temporal drift, which is also known in gyro systems in aviation. This on principle requires from time to time a re-calibration to a fixed coordinate system. However, within the short measuring periods involved in recording the 3D data of the craniomandibular system, this drift is so small that corrections are not really necessary.

For when patient movements are not negligible, the invention intends that the further inertial platform on the patient's head, i.e. in a stationary location relative to the maxilla of the craniomandibular system, be used to measure the movement that took place during the measuring period. Thus the patient's head movement can be measured separately from the actual movement of the measuring device.

For when patient movements are not negligible, the invention intends that the further position finding sensor (inertial platform) on the patient's head, i.e. in a stationary location relative to the maxilla of the craniomandibular system, be used to measure the movement that took place during the measuring period. Thus the patient's head movement can be measured separately from the actual movement of the measuring device.

For this purpose, a frame such as a spectacle frame may be used. It is also possible to use a facebow for mounting the second sensor. Alternatively, a bite fork with an inertial platform may be attached to the maxilla or mandible.

Another option is that a bite block, which contains the at least one second inertial platform, is placed between the dental rows and the patient is requested to close the dental rows.

It is particularly intended that the positional data of the first inertial platform, be linked as first coordinates with second coordinates represented by the positional data of the optional at least one second inertial platform, and that the linked coordinate data be used to generate coordinates for the first sensor and the at least one second sensor in a common coordinate system, in which the coordinates of positions or regions of the craniomandibular system are determined.

For measurements at the mandible it is preferable to attach one further inertial platform in a location stationary relative to the mandible. This for example can be accomplished using a bite block or a bite fork attached to the mandible. Unfavorable space conditions may make it necessary in clinical application to do without a stationary positioning relative to the mandible of the at least one inertial platform. This is practicable if determining a position within the chewing plane is sufficient. In this case it is possible to assume, taking into account the movement of the mandible relative to the maxilla, that the mandible moves relative to the maxilla along an arc-shaped path of motion that is governed by the temporomandibular joint. Measuring a measuring point, e.g. between teeth 31 and 41 during the opening motion of the mandible reveals the motion of the mandible. Every other point of the mandible will travel on a similar—in the mathematical sense—curve. Further, one can take into account a typical mouth opening size to perform an additional rough estimate.

To a first approximation, the position of a gingival pocket will always travel on the same arched path.

Because of the inertial platform that is fixed to the measuring device (intraoral scanner) and provides position-change data (either without or much more precisely with a further inertial platform arranged stationary relative to the maxilla), one knows the current rough position of the scanning sensor relative to the craniomandibular system and the positional change relative to earlier positions. This makes it possible to speed up the merging of individual 3D data sets or, in some cases with difficult geometry, to make it possible at all, since the employed algorithms have difficulties in particular in the rough determination of the relative positions of two or more individual data sets. If the rough position is known, the following fine-adjustment of the data sets relative to each other can be accomplished much simpler and faster, so that the scan results can be linked with relatively low computational effort.

The invention makes available an intraoral scanning system that comprises a device for determining rough positions and the changes in these positions relative to the craniomandibular system.

In accordance with an independently inventive suggestion, the intraoral measuring device is not only used for scanning a dental arch or a section thereof—in order to determine the position of teeth or regions that are to be provided with dental reconstructions—, but also to measure the depth of gingival pockets or the position and extent of dental caries or plaque.

The latter is of importance particularly if it is intended for example to measure gingival pockets, i.e. their depth, without the usual recording of data by calling out the measuring points. Rather, if the starting position of a gingival pocket or region of a gingival pocket of a tooth is known, measurements of regions of the gingival pocket of the same tooth and adjacent teeth can subsequently be performed automatically and consequently recorded, since the location of the resulting positional coordinates is determined from the position of the measuring device, i.e. the first sensor (inertial platform), in relation to the at least one second sensor arranged stationary relative to the maxilla.

In accordance with the invention this can be performed fully-automatically or semi-automatically. If a pocket-depth-measuring section of the measuring instrument is pushed into the pocket, then owing to the teaching according to the invention, the position of the measuring device can be determined and recorded automatically. During semi-automatic measuring it will only be necessary to take a reading of the pocket depth on the measuring device (e.g. on the scale of a probe extending from the measuring device) and to transmit the reading to the patient documentation software on the PC, e.g. by means of a voice-recognition system. The position of the measuring device itself is acquired automatically. In order to facilitate automatic position finding, a starting position must be specified, e.g. contact with the gingiva approximal between teeth 31 and 41. Once this position is known, then owing to the teaching according to the invention, during any movement of the measuring device the new position is determined automatically relative to the first position, so that the position of each measuring point can be acquired automatically. As mentioned above, in the semi-automatic acquisition it is only necessary to enter the pocket depth into a computer for each measurement, e.g. via a computer keyboard or voice-recognition software, while the position itself is stored automatically.

In addition to automatically determining the position of the measuring location, the measuring process itself can also be performed automatically without the need to read off data. This as well is to be seen as an independently inventive suggestion. This can be accomplished in various ways, e.g. using a drag indicator with an electronic read-out (e.g. Florida probe), or pocket-depth measurements using ultrasound, or opto-electronic or impedance-change methods.

Measurements obtained with a method of this type can then be stored automatically together with the positional information in a patient management system.

In particular, the measuring of pocket depths is performed by means of an optical light guide, in the form of one or several fibers of a material transparent to electromagnetic radiation, e.g. glass, sapphire, or plastic, which is inserted into the pocket. The diameter of the optical light guide may be in the region of between 50 μm and 1000 μm without this restricting the teaching of the invention. As soon as the optical light guide penetrates into the pocket, the light intensity and spectral distribution of the light, which is collected by the light guide along its front face and is transmitted to a receiver, are modified by the optical characteristics of the gingiva and the tooth. From this one can determine the penetration depth of the tip of the light guide into the pocket, whereby the measurement is terminated when the front face of the light guide touches the bottom of the pocket. The pocket depth is subsequently calculated as the difference between the position where entry into the pocket was detected and the position where no further movement along the z direction (along the depth of the pocket) takes place.

The light captured by the light guide may be ambient light, which is emitted by for example the lighting of a dentist's chair. But it is also possible to conduct light through the light guide itself and to measure the light reflected at the fiber end by means of a photodiode or another light detector.

A further option is to measure the light backscattered into the cladding of the light guide, or changes in that light.

According to a further proposal at least two optical guides are inserted into the pocket, whereby light is emitted by one or several guides and light is received and subsequently analyzed via at least one other guide. This increases the detection sensitivity of the reflected signal, and different numerical apertures, light guide diameters, and distances between light guides may be used to select a region from where the light reflected into the light guide preferably is to be received. When using several light guides, the spacing between light guides preferably should correspond to 0.5 to 3 times the light guide diameter, but need not be limited to this.

It is also possible to use a coaxial arrangement of a small light guide tube and light guide loosely inserted into the small tube.

According to a different proposal it is intended to use a light guide whose cladding and coating has been removed and whose core has been roughened. The roughened light guide subsequently is housed in an air jacket or at least a coating of a material with a low refractive index x with x<<1.3. A design of this type ensures that the optical fiber in its roughened region has nearly isotropic emissions.

Alternatively a small rod of a scattering medium can be attached to the end of a fiber, which for an adequate choice of the scattering coefficient ($0.1/mm < \mu s < 100/mm$) will also generate a light intensity that is most homogeneous along the length of the small rod.

Now one has the option of charging the fiber with light of one or several wavelengths, by means of for example an LED, a laser diode, or another light source. If necessary it is also possible not to illuminate the fiber, but use it to only pick up ambient light. Measurements of this type may be subject to errors.

If the fiber is charged with light, then this will be emitted more or less isotropically from the roughened end and the corresponding reflected light is gathered. As soon as the roughened region penetrates into the pocket, the reflection rate will change from that of a fiber to air reflection to that of a fiber to tissue reflection and the reverse case. This results in a change in intensity and spectral distribution of the reflected light. The degree of change corresponds to the penetration depth of the sensor into the gingival pocket. The sensor is active at all times and directly detects the penetration into the pocket. The deeper the sensor is located inside the pocket, the more noticeable will be a signal change.

For the purpose of increasing the sensitivity it is also possible to use two corresponding fibers that are surrounded by air or sheathing with a very low refractive index, whereby one fiber serves as sensor and the other fiber as receiver with regard to their roughened regions. Direct light transfer from the transmitter to the receiver is prevented by screening between the sensors. In this case the light guide acting as the receiver only detects light reflecting from tooth or tissue, whereby the reflected light will be attenuated and diffracted differently for each wavelength, making it possible to draw conclusions about the characteristics of the tissue or tooth that the light passed through or that reflected the light. Differences between the wavelengths increase in dependence on the penetration depth of the fiber into the material.

Measurements of the spectrum of the backscattered light can also be used to determine whether the tissue or gingiva is inflamed. The perfusion of the tissue with blood changes in dependence on the extent of the inflammation. The optical characteristics of blood are different from those of the tissue. The extent of perfusion can be determined if one uses applied light of suitable wavelengths. For reference one can use two components of the tissue, namely proteins and water, whereby proteins show a noticeable absorption of wavelengths below 350 nm and water for those above 1500 nm. The absorption maximum of blood is at approximately 400 nm with moderate absorption taking place in the range between 650 nm and 1000 nm. Measuring the ratio of the reduced blood absorption in the wavelength regions <350 nm and >1500 nm relative to the significant blood absorption in the wavelength region 400 nm to 1000 nm allows conclusions to be drawn about the blood perfusion in the tissue. Methods relating to this can be combined in any manner with the determination of gingival pocket depth by means of optical fibers.

However, it is also possible to determine the pocket depth via impedance measurements. An electrically conducting tip, such as e.g. a periodontal probe, can be inserted into the pocket while simultaneously measuring the resistance of the tissue. As soon as the tip of the probe comes into contact with crevicular fluid, the resistance will drop, e.g. to a value lower than 200 k$\Omega$. The resistance in air is greater than 1 M$\Omega$. The penetration depth of the tip into the pocket subsequently is determined by moving the sensor in order to calculate the pocket depth in this manner. Also used may be a bipolar needle that is coated with a saliva-repellent surface such as Teflon.

Alternatively it is possible to use a non-conducting probe body that in some regions is equipped with conducting annular sections at different distances from the probe tip. During the penetration of the probe into the pocket, one ring after another is covered by fluid and the impedance between the rings changes. Also feasible is the performance of capacitive measurements.

It is also possible to measure the gradual immersion of the probe into the periodontal pocket by means of layer with average or high resistance per unit length that is applied onto the probe. Here one uses the characteristics of a potentiometer.

An independently inventive teaching allows determining the location or a real extent of dental caries or plaque by means of the first inertial platform. In this, one utilizes the different reflection characteristics of dental caries or plaque in comparison to healthy tooth regions.

Also possible is the detection/acquisition of the movement of the mandible relative to the maxilla, if one inertial platform is attached to the head of the patient and one further inertial platform is attached to the mandible. In particular, this allows performing dynamic occlusion measurements.

Further details, advantages, and features of the invention are not only found in the claims and the characteristic features contained therein, on their own and/or in combination, but also in the following description of preferred embodiment examples illustrated in the figures.

DETAILED DESCRIPTION OF THE INVENTION

Figure 1:
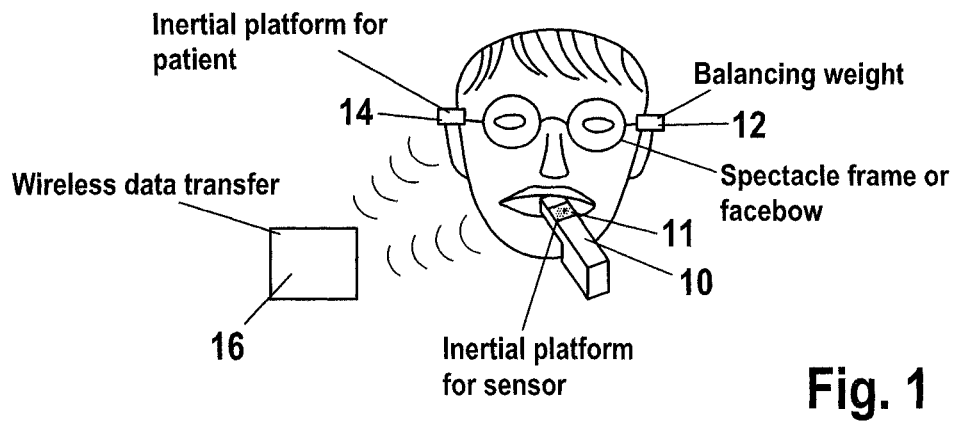
FIG. 1 shows a schematic illustration of first and second inertial platforms that are aimed at a craniomandibular system.

FIG. 1 purely schematically shows a measuring device to be referred to as an intraoral scanner 10, into which is integrated an inertial platform (first sensor), which allows detection of the position of the measuring device in dependence on its motion along the X, Y, and Z directions as well as rotation about the respective axes. The inertial platform may be based on for example an ADIS 16355.

The position of the measuring device 10 and thus the first inertial platform 11 is determined relative to the position of at least one second inertial platform 14 by means of a computer 16, to which the data of the first inertial platform 11 and the second inertial platform 14 are transmitted, ideally in a wireless fashion. The second sensor 14 also contains an inertial platform. The second inertial platform 14 may be integrated into the temple arms of spectacles or in a facebow, or into bite blocks that can be positioned between the mandible and maxilla. A balance weight 12 is attached to the spectacle frame to realize a symmetrical weight distribution.

Figure 2:
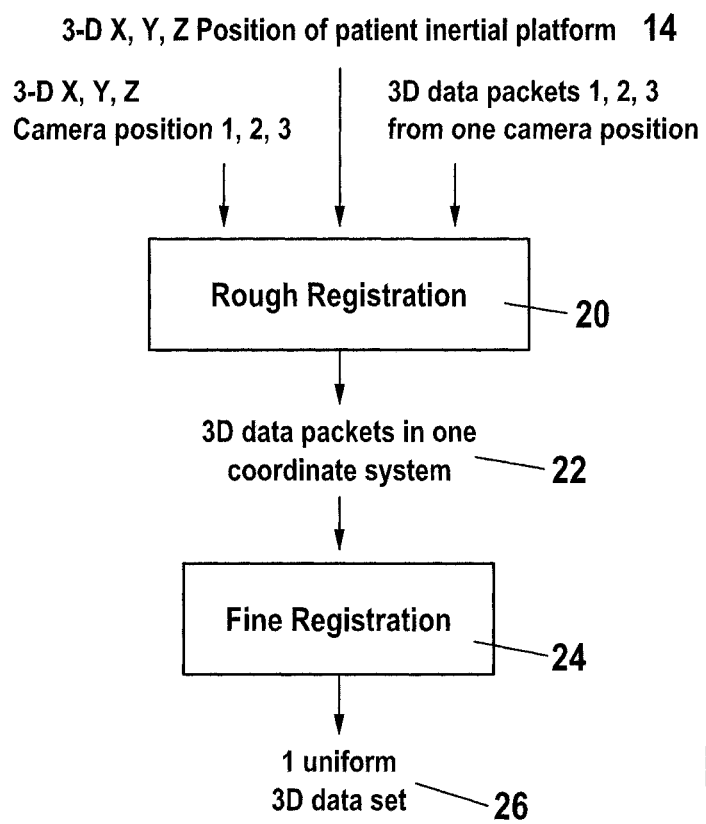
FIG. 2 shows a flow chart.

Thus the computer uses the data of the first inertial platform 11 and the second inertial platform 14 positioned stationary relative to the maxilla to determine the positions of the intraoral scanner, and links them with the 3D data measured at the respective positions. This speeds up the rough positioning of the individual data sets within the common coordinate system (step 20 in FIG. 2). After step 20 the 3D data sets are located within a common coordinate system (step 22). Subsequently performed are fine adjustments to find the best-possible position of the data sets relative to each other (step 24). The uniform 3D data set 26 obtained in this manner now can be used in the manufacture of dental prostheses after further known steps.

The invention's method offers significant savings in computing time, in particular for the digital representation of regions of the mandible and/or maxilla, and avoids incorrect representations, since the positions of the intraoral scanner relative to a region to be scanned are determined at least roughly by the inertial platforms or corresponding position-finding means with equivalent technical effect, which simplifies the task of registering the partial data sets obtained at different viewpoint angles. This rules out incorrect assignments that would be possible with completely unknown scanner positions.

In accordance with the embodiment example that employs two inertial platforms, the first inertial platform transmits data (acceleration values) that are used to compute the change in location of the measuring device relative to the previous measuring location. The second inertial platform transmits data that allow drawing conclusions on the change in position of the patient relative to the patient's original position.

Naturally it is still within the scope of the invention to employ only one inertial platform that determines data related to the change in position between the individual measuring locations. This is accomplished on the basis of the data detected by the inertial platform, i.e. the recording of acceleration values, which in combination with their progression over time allows the computation of the resulting change in position.

On principle, no absolute positions are detected in the 6 degrees of freedom. However, absolute positions can be determined in relation to a known starting position.

In order to measure the depth of gingival pockets at different positions of a tooth, the method according to the invention, i.e. the determining of the positional location of the measuring device 10, can be employed using the first inertial platform on its own or in combination with a or the second inertial platform 14, whereby a sensor element, such as a pin or optical guide, extending from the measuring device 10, is used to measure the pocket depth. But it is also possible to determine the pocket depth using ultrasound, in which case the transmitter and receiver originate from the sensor. The pocket depth also can be measured by means of impedance metering.

Figure 3:
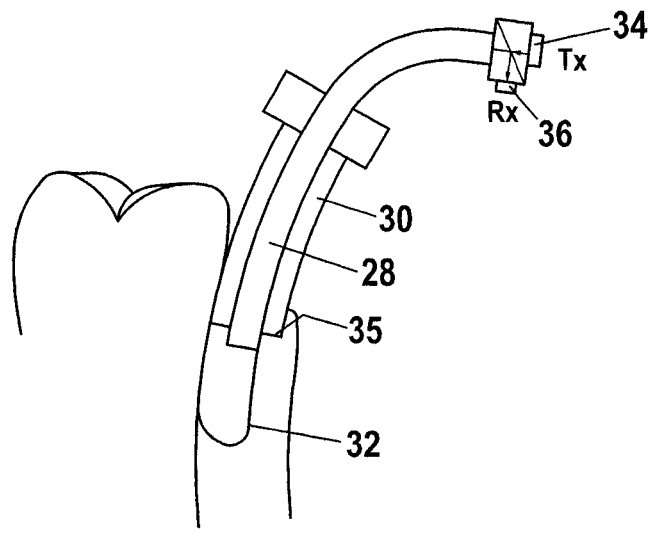
FIG. 3 shows a first embodiment of an arrangement for measuring the depth of a gingival pocket.
Figure 4:
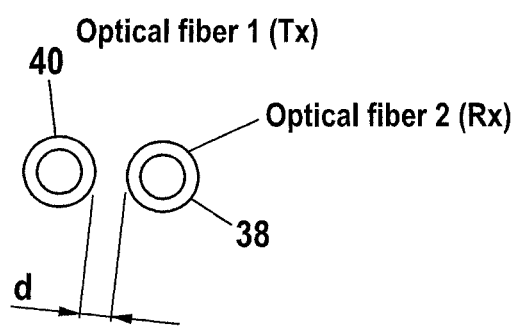
FIG. 4 shows a further schematic illustration of measuring sensors.

However, the measurement preferably is performed opto-electronically. In accordance with FIG. 3, an optical guide in form of an optical fiber 28 consisting of plastic or glass is surrounded by a light-conducting coating 30. The light guide subsequently is inserted into a gingival pocket 32. Light from a light emitter such as at least one light-emitting diode or laser diode 34 is emitted via the light guide, and subsequently radiation reflected in the pocket 32 is guided back to the light sensor 36 via the fiber 28. For short distances, it is also possible to guide the reflected light back to a receiver via coupling into the front face 35 of the coating 30. This entails the advantage of spatially decoupling the light paths of the transmitter and receiver. At the point in time when the front face of the fiber comes into contact with the gingiva, i.e. enters the gingival pocket, the reflected light shows changes in its intensity and—if more than one wavelength is used—also its spectrum. Consequently the time of entry into the gingival pocket is known. The movement along the pocket direction terminates at the bottom of the pocket. The distance traveled since the time of entry corresponds to the pocket depth and can be determined by means of the known positional data from the inertial platform.

It is also possible to insert two optical guides 38, 40 side by side into a pocket, whereby light is introduced via one guide, e.g. the optical guide 38, so that the optical guide or fiber 40 can gather radiation reflected in the pocket, or by the tissue, or by the tooth bordering the pocket, and feed it to a receiver for interpretation. The separation d between the guides 38, 40 should preferably be 0.5 to 3.0 times as large as the diameter of each guide 38, 40.

Figure 5:
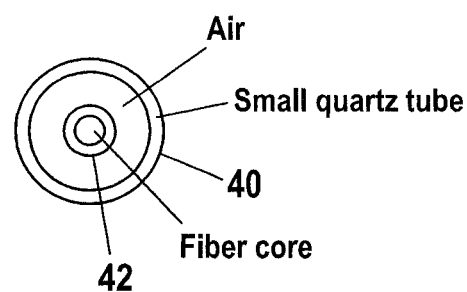
FIG. 5 shows a third embodiment for measuring the depth of a gingival pocket.

As illustrated in FIG. 5 it is also possible to use a coaxial embodiment. A light guide 42 is positioned inside a small tube 40 of glass, sapphire, or quartz so that it is not in contact with the interior surface of the small glass tube. As soon as the assembly comes into contact with the gingiva or is immersed into the gingival pocket, the intensity and spectral distribution of the light guided back through the material of the small tube will change. To prevent liquid from penetrating into the air gap 40a, the assembly is sealed with a transparent window of the same material as the material of the small tube.

Figure 6:
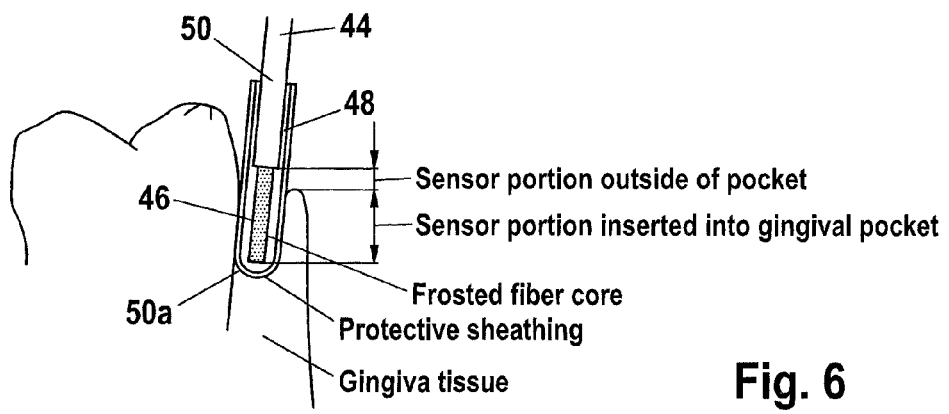
FIG. 6 shows a fourth embodiment for measuring the depth of a gingival pocket.

The embodiment example shown in FIG. 6 employs a light guide 44 that is roughened in its end region 46. For this purpose both the cladding 48 as well as the coating 50 of the light guide are removed. The roughened end region 46 subsequently is arranged inside an enveloping element 50a and is arranged with clearance to its inner surface, whereby the space in between is filled with air. This results in a sudden change in the refractive index, which allows a nearly uniform light emission. Instead of using an enveloping element 50a with air gap it is also possible to coat the roughened section 46, for example with a material having a low refractive index such as Teflon.

The roughened region offers the advantage of nearly isotropic emission of light and of nearly isotropic gathering of reflected light. As soon as the roughened region is pushed into the pocket, the optical characteristics of the periodontal tissue traversed by the light will change the amount and spectral distribution of the backscattered light in dependence on the penetration depth into the periodontal pocket.

In this manner it is not only possible to determine the pocket depth, but also to detect possible inflammation of the gingiva. For this purpose the light guide is charged with radiation of a wavelength region in which the components characterizing the tissue, i.e. protein and water or blood, absorb the radiation to a particularly high degree. Subsequently, ratios of intensities in characteristic absorption regions are compared to infer results on the type and extent of the inflammation.

Figure 7:
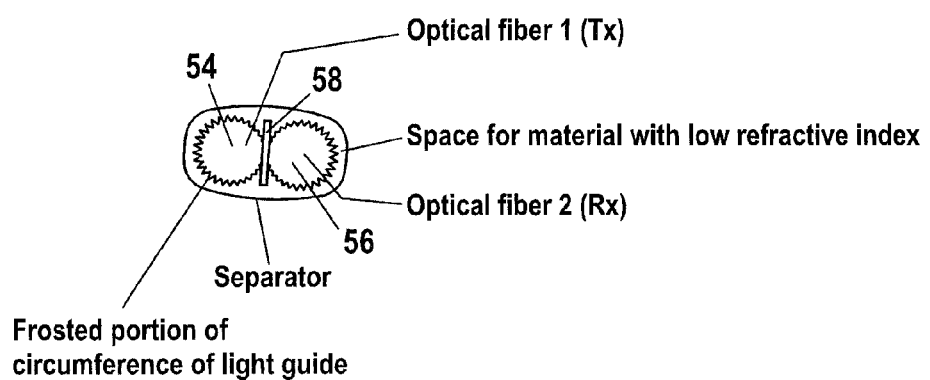
FIG. 7 shows a fifth embodiment for measuring the depth of a gingival pocket.

FIG. 7 illustrates an embodiment version in which—in accordance with FIG. 6—a light guide 54, which has been stripped of coating and cladding at its roughened end, guides and emits radiation into the region of interest to be measured and a light guide 56 prepared in the same manner gathers radiation reflected from the region and feeds it to a receiver. In this the active, i.e. roughened, regions of the light guides 54, 56 should be optically separated or shadowed. Because of this screening, the light must travel a further distance through the tissue. Consequently this arrangement becomes more sensitive to variations in the optical characteristics of the tissue and to the penetration depth into the gingival pocket.

It is also possible to perform measurements of impedance to determine the pocket depth. For this one can employ a conducting tip, such as the tip of a periodontal probe, with impedance that varies in dependence on contact with crevicular fluid. When the tip is not in contact with fluid but rather moves through air, the resistance will be greater than 1 MΩ. At the very moment that contact is established with the fluid in the gingival pocket, the resistance drops to values of less than 200 kΩ. This change in resistance is used as an indicator of penetration into the pocket. Subsequently the tip is moved into the pocket and all the way to the bottom and the shifting distance is determined by means of the first sensor equipped with the inertial platform, in order to automatically determine the depth. The end point is considered reached when the motion into the pocket stops.

Figure 8:
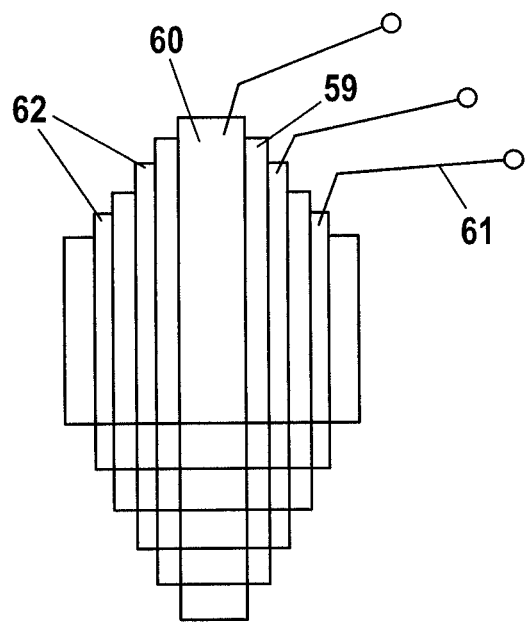
FIG. 8 shows a sixth embodiment for measuring the depth of a gingival pocket.

Another option is to insert into the pocket a tip that is equipped with electrodes in planes that extend in parallel and are electrically insulated relative to each other, whereby the tissue and the fluid present in the pocket will create an electrically conducting connection between the electrodes. A corresponding design is shown in FIG. 8. Around a conducting core 60 are grouped alternating insulation layers 59 and conducting layer 62. This creates conductive annuli, each of which is equipped with its own pad electrode 61. If the insulation layer between the electrodes is wetted by a conductive fluid or if tissue comes into contact with two neighboring electrodes, the resistance between these two electrodes drops significantly, allowing a stepwise measurement of the penetration depth of the probe into a fluid or into the periodontal pocket. A practical design version can resolve changes in penetration depth of 0.5 mm-1 mm. In order to be able to perform a depth measurement, the free ends of the conducting core 60 or the conducting layers terminate in different planes, as is indicated in the figure.

Pockets can also be measured by way of a capacitive measurement. For this purpose two or more electrodes 64 are arranged on opposite sides of a small carrier rod 63 of a material having a low dielectric coefficient, e.g. Teflon or polypropylene, which in combination with the tissue that the probe is immersed in form a capacitor. The electrodes 64 are coated by a preferably hydrophobic insulating layer and are connected to evaluation electronics via connecting leads 67. The capacitance of the assembly changes in dependence on the immersion depth 65.

Figure 9:
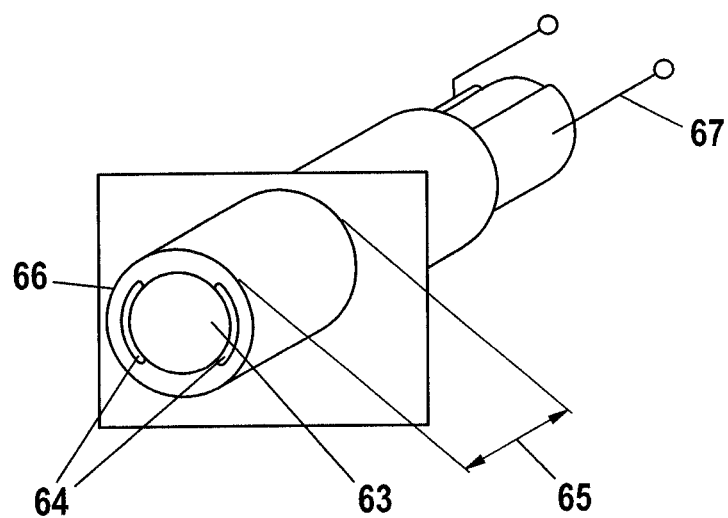
FIG. 9 shows a seventh embodiment for measuring the depth of a gingival pocket.

If—as in the embodiment version according to FIG. 9—the insulation 66 is removed and the electrodes 64 are produced from a medium to high resistance material it is possible to determine the immersion depth from the continuous change in resistance of the assembly.

The intraoral scanner 10 not only can be used to automatically determine positions in the craniomandibular system or regions of the craniomandibular system, such as local arrangements of teeth or measuring points with simultaneous depth measurement of a gingival pocket, but it is also possible to determine the position and extent of dental caries or plaque. For this one utilizes the difference in reflection spectra of a healthy tooth compared to regions affected by caries or plaque, which can be evaluated together with the position finding of the first sensor.

The invention claimed is:

1. A method for determining the position of a measuring device for measuring a depth of gingival pockets and/or detecting dental caries or plaque, wherein the measuring device measures intraorally, is movable relative to a patient's craniomandibular system, and is used to measure positions in the craniomandibular system or regions of the craniomandibular system, said method comprising the steps of:

providing a first inertial platform and at least one second inertial platform, determining the position of the measuring device using the first inertial platform arranged in a stationary position relative to the measuring device, and at least one second inertial platform arranged in a stationary position relative to the maxilla of the craniomandibular system, triggering a starting signal, synchronously evaluating positional data of the first inertial platform and the at least one second inertial platform after the starting signal is triggered;

wirelessly transmitting data from the first inertial platform and the second inertial platform to a computer, to determine the position of the measuring device; and measuring the depth of the gingival pockets and/or detecting the dental caries or plaque.

2. A method for determining the position of a measuring device for measuring a depth of gingival pockets and/or detecting dental caries or plaque, wherein the measuring device measures intraorally, is movable relative to a patient's craniomandibular system, and is used to measure positions in the craniomandibular system or regions of the craniomandibular system, said method comprising the steps of:

providing a single inertial platform, determining the position of the measuring device using the inertial platform arranged in a stationary position relative to the measuring device, wherein the position of the measuring device is determined using the inertial platform arranged relative to a starting point used as a starting signal, wherein said starting point is in a stationary relation to the craniomandibular system; and measuring the depth of the gingival pockets and/or detecting the dental caries or plaque.

3. The method of claim 1, characterized in that the positional data of the first inertial platform are linked as first coordinates with the positional data of the at least one second inertial platform as second coordinates, and from the linked data are generated coordinates in a common coordinate system for the first inertial platform and the at least one second inertial platform, in which coordinates of positions or regions of the craniomandibular system are determined.

4. The method of claim 1, characterized in that, the positions or coordinates of the first inertial platform are determined using the at least one second inertial platform that is arranged on the head of the patient.

5. The method of claim 1, wherein the at least one second inertial platform is attached to a frame, or in a bite block that is arranged between the mandible and maxilla.

6. The method of claim 1 or 2, characterized in that for determining position coordinates of regions of the mandible, the movement of the mandible along an arch extending from the maxilla is additionally taken into account.

7. The method of claim 1, characterized in that for determining the position coordinates of regions of the mandible and/or maxilla, one additional or the first inertial platform is arranged in a position that is stationary relative to the mandible or maxilla.

8. The method of claim 1, characterized in that for determining a position of the mandible or the coordinates of said position, a third inertial platform equipped with an inertial platform is arranged in a position that is stationary relative to the mandible.

9. The method of claim 1 or 2, characterized in that the measuring device is used to measure the pocket depth of a tooth.

10. The method of claim 9, characterized in that the pocket depth is determined using ultrasound, drag indicator, opto-electronic, inductive, capacitive, or resistance measurements.

11. The method of claim 1 or 2, characterized in that the measuring device comprises a pin-shaped element that is used to measure gingival pockets.

12. The method of claim 11, characterized in that the depth of the gingival pocket and/or the position and extent of dental caries or plaque are measured electrically and/or opto-electronically using the pin-shaped element, by varying the position of the measuring device.

13. The method of claim 9, characterized in that the measuring device is used to measure the pocket depth in dependence on the position of the first inertial platform relative to the at least one second inertial platform.

14. The method of claim 9, characterized in that an optical light guide is inserted into the pocket and the depth of the pocket is determined in dependence on light fed via the optical light guide to a receiver.

15. The method of claim 14, characterized in that changes in intensity and/or spectral distribution of the light directed to the receiver via the optical light guide are analyzed to determine the pocket depth.

16. The method of claim 9, characterized in that in measuring the pocket depth, one optical light guide is used for illumination and for returning the backscattered light.

17. The method of claim 14, comprising analyzing ambient light received by the optical light guide to measure the pocket depth.

18. The method of claim 14, characterized in that the optical guide is surrounded by a light-conducting cladding and light coupled-in via a front face of the optical guide is analyzed to measure the pocket depth.

19. The method of claim 9, characterized in that at least two optical light guides are inserted into the pocket, whereby light is supplied via one guide and light received via the other guide is evaluated.

20. The method of claim 14, characterized in that a fiber or fiber bundle is used as an optical guide, whereby the optical guide has a diameter D, with 50 µm≤D≤1000 µm.

21. The method of claim 19, characterized in that when using two optical light guides, these are positioned with a clearance D between them, with $0.5D \leq d \leq 3D$, where D represents the diameter of the optical light guide.

22. The method of claim 9, characterized in that the optical light guide is positioned in a coaxial arrangement inside of a transparent small tube, without coming into contact with the small tube.

23. The method of claim 9, characterized in that, the optical guide is a light-conducting fiber that at its free end has been freed of cladding and coating and has been roughened, that the optical guide is charged with light of a selected wavelength region, in the region of 350 nm≤λ≤10,000 nm, and that the light reflected back into the optical guide via the roughened end is analyzed to determine the pocket depth.

24. The method of claim 9, characterized in that the change in intensity and/or spectral distribution of the received light is analyzed to determine the pocket depth.

25. The method of claim 9, characterized in that two optical guides that are roughened in some regions are inserted into the pocket, light is directed into the pocket via one guide and light reflected in the pocket is directed to a receiver via the other guide.

26. The method of claim 19, characterized in that roughened regions of the optical guides are screened relative to each other.

27. The method of claim 14, characterized in that light fed to the receiver via the optical light guide is evaluated with regard to the absorption characteristics of the pocket.

28. The method of claim 14, characterized in that one determines the ratio of absorption of radiation in the wavelength region $\lambda_1$, $\lambda_2$, with $\lambda_1 \leq 350$ nm and $\lambda_2 > 1500$ nm, relative to the absorption of radiation in the wavelength region $\Delta\lambda$, with 400 nm≤$\Delta\lambda$≤1000 nm.

29. The method of claim 9, characterized in that the change in resistance of a conducting measuring sensor as the measuring device introduced into the pocket, is measured in dependence on its penetration depth into the pocket.

30. The method of claim 1, characterized in that a measuring sensor as the measuring device, which consists of an electrically insulating material and comprises spaced-apart electrode sections that are arranged in planes of equal cross-section of the measuring sensor, is inserted into the pocket, and a change in impedance between the electrode sections is measured to determine the pocket depth.

31. The method of claim 1, characterized in that a measuring sensor of an electrically insulating material with spaced-apart band-like electrode sections extending along the sensor's longitudinal direction, as the measuring device, is inserted into the pocket, and a change in impedance between the electrode sections is measured to determine the pocket depth.

32. The method of claim 30, characterized in that the measuring sensor is coated with a hydrophobic coating.

33. The method of claim 9, characterized in that an optical guide is inserted into the pocket and spectral distribution of the received radiation is evaluated by the measuring device to determine the location and/or extent of dental caries and/or plaque.

34. The method of claim 1, characterized in that the movement of the mandible relative to the maxilla is measured, whereby one inertial platform is attached to the head of the patient and one further inertial platform is attached to the mandible.

35. The method of claim 1, further comprising:
providing a computer;
transmitting positional data of the first inertial platform and the at least one second inertial platform to the computer; and
using the computer to analyze the transmitted positional data, to determine the position of the measuring device and the first inertial platform relative to the position of the at least one second inertial platform.

* * * * *